(12) United States Patent
Lasalde-Dominicci et al.

(10) Patent No.: US 10,155,221 B1
(45) Date of Patent: Dec. 18, 2018

(54) HIGH-THROUGHPUT CRYSTALLOGRAPHIC SCREENING DEVICE AND METHOD FOR CRYSTALIZING MEMBRANE PROTEINS USING A SUB PHYSIOLOGICAL RESTING MEMBRANE POTENTIAL ACROSS A LIPID MATRIX OF VARIABLE COMPOSITION

(71) Applicants: Jose A. Lasalde-Dominicci, San Juan, PR (US); Orestes Quesada-Gonzalez, Canovanas, PR (US); Josue Rodriguez-Cordero, Carolina, PR (US); Carlos Baez-Pagan, Carolina, PR (US)

(72) Inventors: Jose A. Lasalde-Dominicci, San Juan, PR (US); Orestes Quesada-Gonzalez, Canovanas, PR (US); Josue Rodriguez-Cordero, Carolina, PR (US); Carlos Baez-Pagan, Carolina, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 15/996,853

(22) Filed: Jun. 4, 2018

Related U.S. Application Data

(63) Continuation of application No. 15/638,276, filed on Jun. 29, 2017.

(51) Int. Cl.
  *C30B 7/12* (2006.01)
  *B01L 3/06* (2006.01)
  (Continued)

(52) U.S. Cl.
  CPC ............ *B01L 3/06* (2013.01); *B01J 19/0046* (2013.01); *C07K 1/306* (2013.01); *C30B 7/12* (2013.01);
  (Continued)

(58) Field of Classification Search
  CPC ............ C30B 29/54; C30B 29/56; C30B 7/12
  See application file for complete search history.

(56) References Cited

U.S. PATENT DOCUMENTS

| | | | | |
|---|---|---|---|---|
| 5,096,576 A | * | 3/1992 | Szabo | A01K 63/045 119/260 |
| 7,229,500 B2 | * | 6/2007 | Haushalter | B01J 19/0046 117/95 |

(Continued)

OTHER PUBLICATIONS

Carina Pareja-Rivera, et al, Recent Advances in the Understanding of the Influence of Electric and Magnetic Fields on Protein Crystal Growth, Cryst. Growth Des., Dec. 6, 2016.

(Continued)

*Primary Examiner* — Robert M Kunemund
(74) *Attorney, Agent, or Firm* — Hoglund & Pamias, PSC; Roberto J. Rios

(57) ABSTRACT

The invention is a high-throughput voltage screening crystallographic device and methodology that uses multiple micro wells and electric circuits capable of assaying different crystallization condition for the same or different proteins of interest at the same of different voltages under a humidity and temperature controlled environment. The protein is solubilized in a lipid matrix similar to the lipid composition of the protein in the native environment to ensure stability of the protein during crystallization. The invention provides a system and method where the protein is transferred to a lipid matrix that holds a resting membrane potential, which reduces the degree of conformational freedom of the protein. The invention overcomes the majority of the difficulties associated with vapor diffusion techniques and essentially reconstitutes the protein in its native lipid environment under "cuasi" physiological conditions.

30 Claims, 16 Drawing Sheets

(51) Int. Cl.
*C07K 1/30* (2006.01)
*G06F 19/16* (2011.01)
*C30B 29/58* (2006.01)
*B01J 19/00* (2006.01)
*G06F 19/00* (2018.01)
*C40B 40/10* (2006.01)

(52) U.S. Cl.
CPC ............. *C30B 29/58* (2013.01); *G06F 19/16* (2013.01); *G06F 19/701* (2013.01); *B01J 2219/00317* (2013.01); *B01J 2219/00605* (2013.01); *B01J 2219/00725* (2013.01); *B01J 2219/00853* (2013.01); *C40B 40/10* (2013.01)

(56) References Cited

U.S. PATENT DOCUMENTS

| | | | |
|---|---|---|---|
| 7,459,021 B2 | 12/2008 | Bukshpan | |
| 8,038,792 B2 | 10/2011 | Bukshpan | |
| 8,252,899 B2* | 8/2012 | Stevens | C07K 14/705 |
| | | | 435/183 |
| 2011/0042215 A1* | 2/2011 | Hou | B01D 9/00 |
| | | | 204/547 |
| 2015/0072900 A1* | 3/2015 | Srinivasan | C07K 1/1136 |
| | | | 506/40 |
| 2016/0208405 A1* | 7/2016 | Yamanishi | C07K 1/306 |

OTHER PUBLICATIONS

Edith Flores-Hernandez, et al., An electrically assisted device for protein crystallization in a vapor-diffusion setup, J. Appl. Cryst. (2013). 46, 832-834.

* cited by examiner

HIGH-THROUGHPUT CRYSTALLOGRAPHIC SCREENING DEVICE AND METHOD FOR CRYSTALIZING MEMBRANE PROTEINS USING A SUB PHYSIOLOGICAL RESTING MEMBRANE POTENTIAL ACROSS A LIPID MATRIX OF VARIABLE COMPOSITION

GOVERNMENT INTEREST

The claimed invention was made with U.S. Government support under grant number R01 GM098343 awarded by the National Institutes of Health (NIH). The government has certain rights in this invention.

BACKGROUND OF THE INVENTION

Approximately 30% of the human genes code for membrane proteins. Despite the efforts made by the best worldwide crystallographers, only minute fraction of the entries in the Protein Data Bank correspond to membrane proteins. A 3D protein structure is critical to the advancement and efficiency of rational drug design, as well as to protein structure-function studies, because the majority of drugs and natural effector molecules stereo-specifically interact with target proteins to affect their physiological and biological activity by blocking or altering its properties.

Membrane proteins have hydrophobic domains and are expressed at relatively low levels. This creates difficulties in obtaining enough protein and growing crystals. The determination of high-resolution structures for these proteins is far more difficult than globular proteins. Nowadays, less than 0.1% of protein structures determined are membrane proteins.

The crystallization process completely depends on the organization ability of the proteins in a medium. Once these proteins are organized repetitively in a solid three-dimensional lattice, it is that the crystal of the protein is formed. This process is regulated by physical-chemical, kinetic and thermodynamic factors and consists of two steps. The first step is known as nucleation, in which the protein molecules that are dissolved in the matrix originally used to collect it from their natural environment, begin to cluster. This gives rise to an extremely small focus, nucleus, on the solution where there is a higher concentration of the protein as a solute. The second step is the continuous and orderly growth of this small focus of crystals. Nucleation can be initiated by the inclusion of a precipitating agent as is the case in the vapor diffusion technique.

During these processes the proteins could diffused and grouped according to the conformation that it acquires both in the extraction matrix used for its production and in the medium in which it is being precipitated. Therefore, the crystals that form, if this occurs, do not necessarily reflect the "true" structure of these proteins in their natural environment. Specifically, many technical problems are associated with the task of membrane protein crystallization. The principal problem with the crystallization of membrane proteins is that they are difficult to handle and solubilize from its native environment in such a way that retains native conformation and activity. Then, the solubilized protein-detergent complex needs to be placed in an environment similar to the native membrane and force nucleation. Membrane proteins are inherently amphiphilic, they comprise hydrophobic and hydrophilic regions. Due to their amphiphilic nature, membrane proteins tend to aggregate rapidly to minimize the hydrophobic regions. The addition of precipitants often causes an interaction with the solubilized protein-detergent complex that induces phase separation. For several decades the crystallization of membrane proteins has been done using vapor diffusion methods including hanging drop and sitting drop. The majority of the crystallization methods using vapor diffusion techniques rely on reducing the solubility of proteins in an aqueous environment, for instance isoelectric focusing methods.

All membrane proteins are embedded inside a lipid membrane that holds a resting membrane potential (RMP). On the basis of this fundamental principle, we believe that the structural conformations of membrane proteins (including ligand gated channels) are voltage-dependent. The most remarkable example for the voltage-dependent conformation of a protein is the large family of voltage-dependent ion channels. Our group further studied this concept while recoding single channel currents (cell-attached) in myocytes. In order to estimate the opening and closing rate constants (at −80 mV), it was necessary to record at least 100 bursts per acetylcholine concentration [ACh]. At high ACh concentrations (>500 µM) the number of bursts per [ACh] was dramatically reduced as a result of desensitization. To overcome this problem, we made a quick change in the polarity of the amplifier (from −80 mV to +80 mV and back to −80 mV in ~1 sec) and the single burst activity recovered immediately. This experiment revealed that at +80 mV the agonist was expelled from the ACh binding site and the channel conformation shifted from the desensitized conformation and immediately equilibrated between the open and closed states until it desensitized again. Thus, even in a ligand-gated channel such as the nAChR, the desensitized conformation can be reversed by changing the RPM. The biophysical principle here is that a membrane protein sits in a voltage gradient across a membrane and some localized domains in the protein can display voltage dependency.

Accordingly, what is needed is a system and a method for the crystallization of membrane proteins without the limitations and constraints of the prior art systems and techniques including vapor diffusion methods and LCP.

SUMMARY OF THE INVENTION

The invention is a high-throughput voltage screening crystallographic device and methodology for protein crystallization which consists of three layers of multiple micro wells electric circuit capable of assaying different crystallization condition for the same or different proteins of interest at different voltages under a humidity and temperature controlled environment.

The methodology of the invention could be used with a single micro-capillary crystal tube of different internal diameters pre-cut for easy recovery of the protein crystal, or it can be configured to allow multiple crystallization conditions in parallel.

According to an aspect of the invention, the crystallization system enables the use of close amphiphilic environments (e.g. monooelein) for membrane protein crystallization and the rates of evaporation are controlled by the relative humidity conditions, which are adjusted in a precise and stable way during the combination of the solubilized protein-detergent complex and amphiphilic reagents.

According to another aspect of the invention, the protein crystals can nucleate and grow under different dehydration conditions.

BRIEF DESCRIPTION OF THE DRAWINGS

Further features and advantages of the invention will become apparent from the following detailed description taken in conjunction with the accompanying figure showing illustrative embodiments of the invention, in which.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Figure 1:
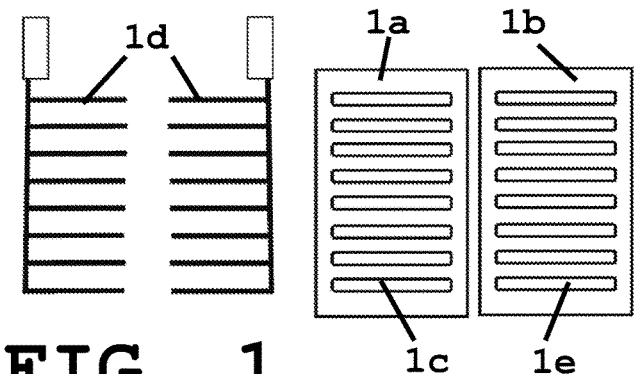
FIG. 1 illustrates the components of the sample unit according to an embodiment of the present invention.
Figure 2:
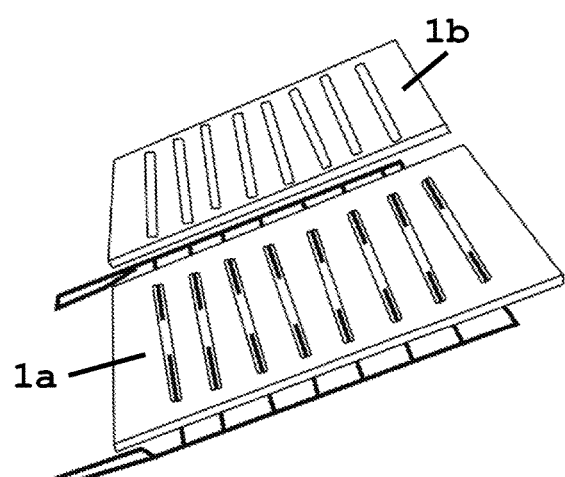
FIG. 2 illustrates the sample unit partially assembled according to an embodiment of the present invention.
Figure 3:
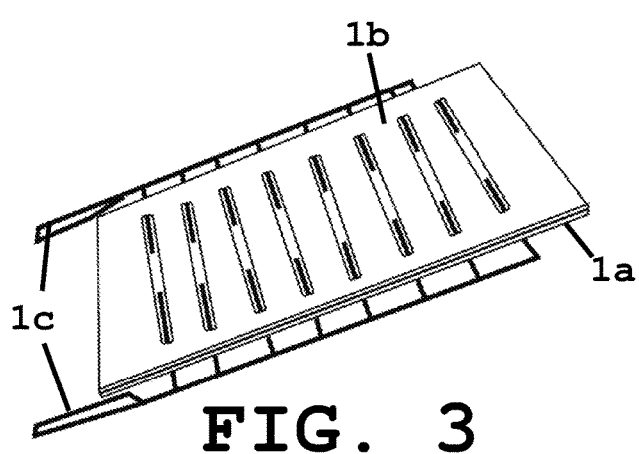
FIG. 3 illustrates the sample unit assembled according to an embodiment of the present invention.
Figure 4:
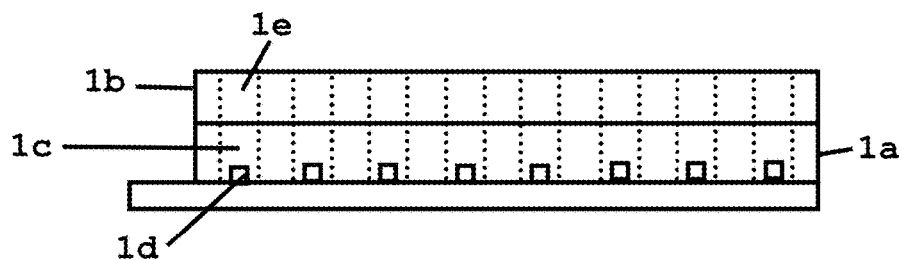
FIG. 4 illustrates a side cross-sectional view of the sample unit according to an embodiment of the present invention.
Figure 5:
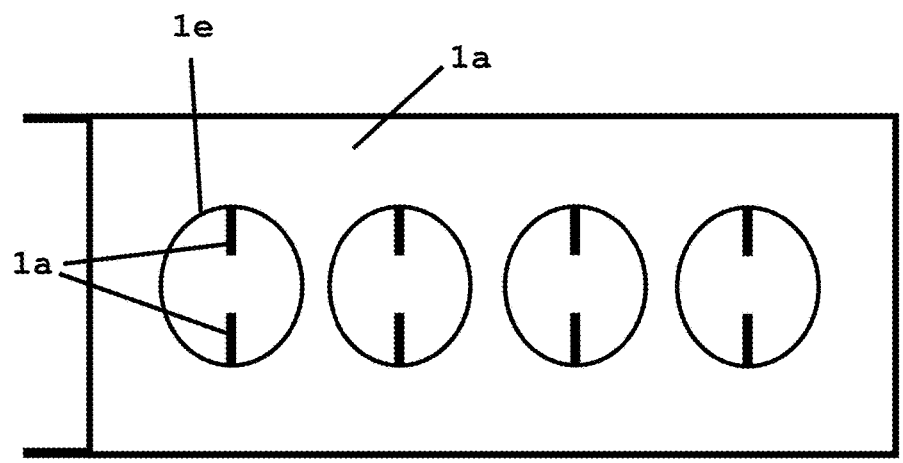
FIG. 5 illustrates a sample unit according to another embodiment of the present invention.

The system of present invention provides a sample unit 1 including a sample holding layer 1a and a lid layer 1b, wherein the sample holding layer 1a includes at least one well 1c with a pair of electrodes 1d and the lid layer 1b also includes at least one well 1e as shown in FIGS. 1-4. Alternatively, depending on the protein loading method the lid layer can be substituted with thin strip of clear adhesive tape. According to a preferred embodiment of the invention, the volume per well in the sample holding layer is 50 μl and 25 μl in the lid layer well. However, other volumes can also be used depending on several factors or parameters such as but no limited to the amount of sample needed. As can be appreciated, the wells have a rectangular shape with the dimensions being selected based on the volume desired to hold the sample for crystallization purposes. In accordance to another embodiment, the wells are provided as round-shaped wells (FIG. 5) with the dimensions also being selected based on the volume desired to hold the sample for crystallization purposes. One advantage of using round-shaped wells is that smaller-volume wells can be provided as the electrodes can be positioned closer to each other requiring smaller voltages and increasing the magnetic field effect during crystallization.

Figure 6:
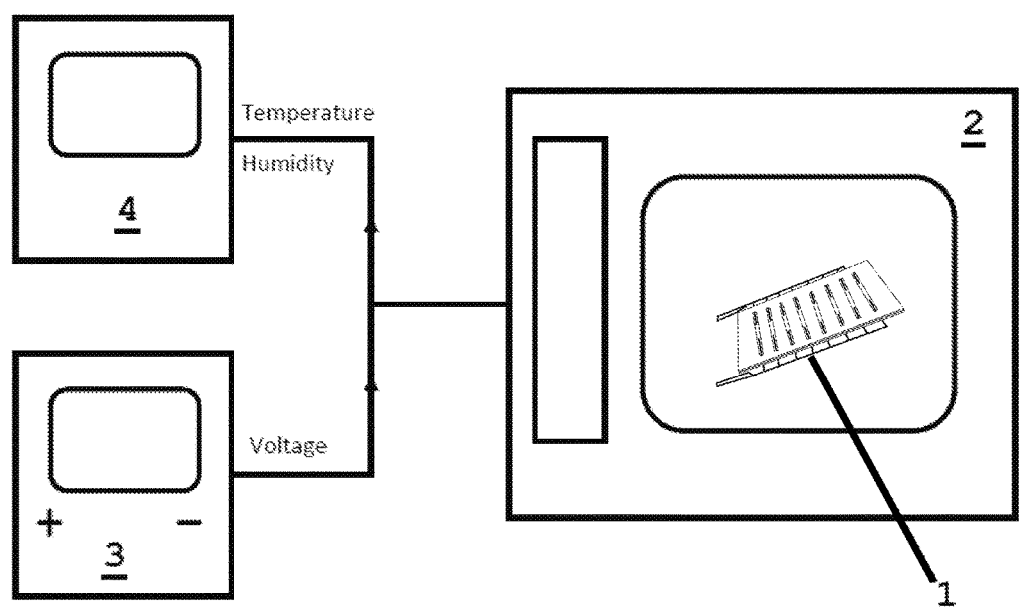
FIG. 6 illustrates a crystallization system according to an embodiment of the present invention.

FIG. 6 illustrates a general crystallization system according to the present invention. An incubator 2 is provided to incubate the sample unit 1 during the crystallization process. A power supply unit 3 is connected to the electrodes of the sample holding layer 1a to provide the required voltage in accordance with the invention. In addition, a temperature and humidity monitoring means 4 is provided to monitor and control the crystallization process within specific temperature and humidity conditions. Other monitoring and control means can be provided to ensure proper crystallization of the proteins in accordance to the method of the present invention. All these components can be provided externally to the incubator 2 or alternatively can be integrated as part of the incubator 2.

One important advantage of the invention is that multiple sample units can be incubated simultaneously while applying a desired voltage and maintaining specific incubation conditions. For example, different protein concentrations can be provided in different sample units or in different wells of the same sample unit. Also, the system of the invention allows to supply the same voltage to all the wells of the sample units or different voltages can be supplied to each well. In addition, with proper control and monitoring different crystallization techniques could be simultaneously carried out in the incubator. The voltage supplied to the sample units can be provided by a single voltage source or via a multi-voltage source. This can be done using plural regulated voltage sources or using a multi-voltage regulated output circuits. It is important to note that the selection of regulated voltage sources as well as the voltage ranges will depend on the type of protein and membrane resistance which determines the range of membrane potentials in which membrane protein crystals are formed in a defined lipid matrix composition also using different electrode diameters. In addition, the resistance of the lipid membrane is critical to assure that ion flux is constant during the crystallization process. Our data shows that crystallization of membrane proteins can occur within a very limited range of sub membrane potentials. As can be appreciated, the system of the present invention is a higly-configurable and flexible system that can be used with different protein crystallization methods and overcomes the majority of the difficulties associated with the typical methods.

In operation, the protein of interest needs to be extracted, purified and properly prepared prior to loading into the sample unit 1. Note that this step will vary depending on several factors including but not limited to: the type and amount of protein, physiological pH of the protein, ionic strength of the medium, optimal crystallization potential, and solubility of the detergent among others. For example, according to an embodiment of the invention, Nicotinic Acetylcholine Receptor (nAChR) extraction was performed by homogenizing 200 g of Torpedo californica tissue. To perform the solubilization of the crude membranes, they were thawed, and mixed with a 1% detergent solution containing DB-1× Buffer (100 mM NaCl, 10 mM MOPS, 0.1 mM EDTA, and 0.02% NaN3). The detergent used to extract the transmembrane proteins was LysoFos Choline 16, Anagrade (LFC-16). After extraction, purification step was carried out using affinity chromatography. During the column's preparation, Bromoacetylcholine bromide was coupled to Affigel 10 (Bio-Rad) with DB-1× as a coupling buffer. The first step of the preparation of Affigel-10 was to incorporate sulfhydryl groups. To do so, 25 ml of Affigel-10, to which the conservator was eliminated through a series of washes in isopropanol and water, was equilibrated with 50 ml of 20 mM MOPS at pH 7.4. Afterwards 50 ml of cysteine 0.054M was added, allowing it to react for one hour. After the cysteine excess was rinsed off with 200 ml of water, 50 ml of the reducing agent dithiothreitol (DTT) 0.1 M with MOPS at pH 8.0 was added for thirty minutes. After equilibration using 100 ml of water, 500 mg of Bromoacetylcholine bromide was added, which attached to the thiol groups in the gel. The remaining thiol groups were blocked with 50 mg of iodoacetamide. Once the Affigel-10 had undergone anhydrous coupling, it was placed in an Econo Bio-Rad 1.5×20 cm column and stored at 4° C. with a low ionic force of 50 mM Sodium Acetate pH 4.0. The solubilized extracts of crude membranes were passed through the column, during which the nAChRs attached to the acetylcholine by affinity. The elution of the chromatographic matrix receptor was performed with a solution containing carbamylcholine, which has greater affinity in the column. This yields an elution solution containing purified nAChRs. All steps were carried out in the cold room (4° C.) or keeping the samples on ice. As can be understood, one skill in the art would know the exact conditions and parameters for protein extraction and purification that would provide the optimal conditions for crystal formation in accordance with the present invention.

Figure 7:
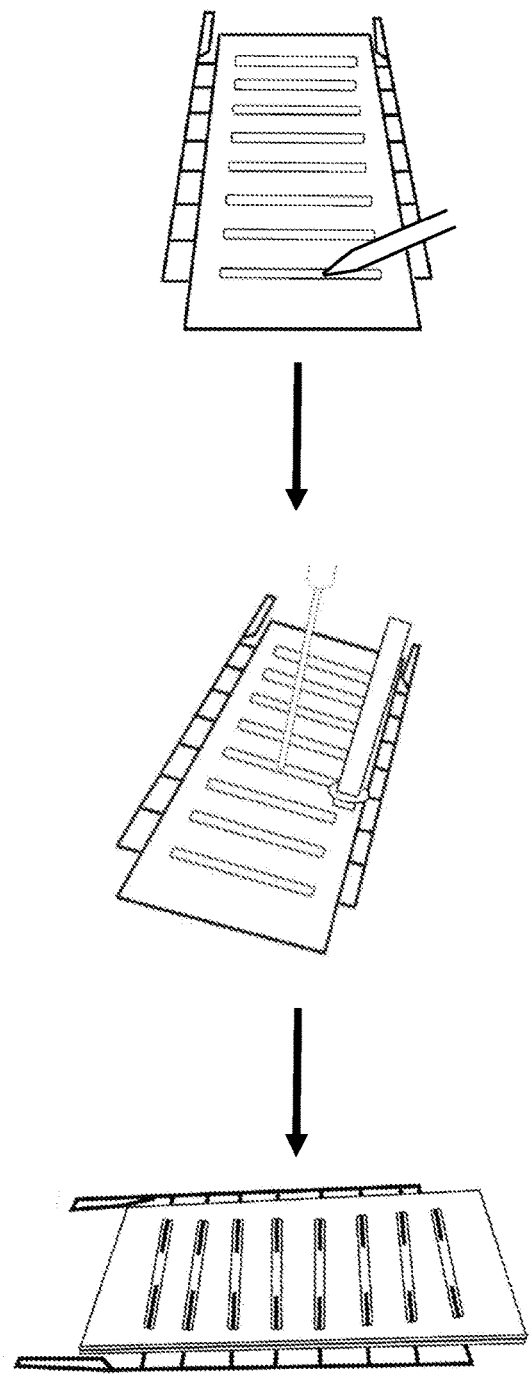
FIG. 7 illustrates the sample unit preparation for a standard protein sample loading according to an embodiment of the present invention.
Figure 8:
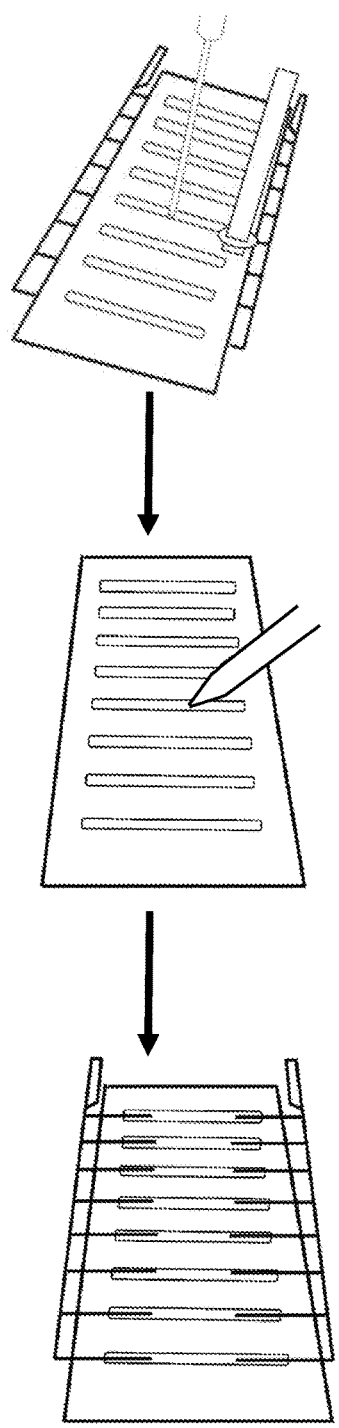
FIG. 8 illustrates the sample unit preparation for a vapor diffusion protein sample loading according to an embodiment of the present invention.

Once the protein has been prepared, it needs to be loaded into the sample units 1 prior to placement inside the incubator 2. This step will vary depending on the type of crystallization desired. FIG. 7 illustrates the steps for a standard protein loading where the crystallization precipitant solution is added to each well 1c of the sample holding layer 1a and the protein sample is later deposited in the center of each well 1c using a dispenser between the circuit electrodes ensuring contact between the electrodes. Afterwards, the sample unit is sealed with the lid layer 1b or alternatively a layer of clear adhesive tape. For a vapor diffusion protein loading, as shown in FIG. 8, the protein sample is deposited in the center of each well 1c of the sample holding layer 1a between the circuit electrodes 1d, wherein the protein sample must be in lipid cubic phase and must be in contact with both circuit electrodes 1d. Then, the crystallization precipitant solution is added to each well 1e of the lid layer 1b and finally the the sample holding layer 1a is turned over or flipped 180° and placed on top of the lid layer 1b to seal the sample unit. It is important to point out that the incubator 2 should be at the desired temperature prior to loading the proteins in the sample units.

The next step is to calibrate and prepare the system for incubation during the crystallization process. To that effect, the voltage source is turned on and adjusted to the maximum voltage value to be applied to the sample units and then while measuring the voltage, adjusting the output voltage to the desired values. Afterwards, the voltage source is turned off and its output is electrically connected to the electrodes arrangement on the sample units inside the incubator 2. The voltage on each well Is measured and adjusted accordingly to ensure the required voltage for crystallization, wherein the incubator is finally closed with the sample units inside ready for crystallization.

Finally, the proteins are incubated for a predetermined amount of time, which according to a preferred embodiment of the invention is between 1-2 weeks. When the crystallization process is finished the voltage supply is turned off and disconnected from the sample units holding the protein crystals for subsequent removal from the incubator and crystal extraction for appropriate analysis.

There are several aspects of the system and methodology to consider when using the present invention for protein crystallization. First, the membrane protein sample to be crystallized in this system must be highly pure to ensure optimal crystallization. Also, the membrane protein is solubilized in a lipid matrix of variable composition at a particular lipid to protein ratio and to ensure stability of the membrane protein, the lipid composition used for the crystallization must be similar to the lipid composition of the protein in the native environment. To that effect, a lipidomic analysis of the model membrane protein must be performed and a lipid matrix containing lipid-detergent analogs similar to the native lipid composition of the protein must be used. In addition, a variety of lipid phases can be used with the invention, which in turn results in a variable degree of hydration. Furthermore, the lipid composition of the matrix can be variable depending on the type of membrane protein sample. In an embodiment of the invention, the resistance of the lipid matrix is in the range of 1-100MΩ. However, other ranges of resistances such as 25-200MΩ can be used depending on the protein size, protein concentration and lipid composition. It is important to point out that the resistance of the lipid matrix (LMx) remains variable in the initial phases of the crystallization, however, it must reach a constant value during the crystallization procedure (24-168 hours). Optionally, at any given point during the crystallization procedure, lipid doping can be performed depending on the resistance of the lipid-protein matrix and the membrane protein. Furthermore, a variable physiological membrane potential (−140 mv-10 mV) can be used to stabilize the membrane protein conformation at the beginning of the experiment and after a period of 1-2 hours the potential can be slowly decreased to reach a sub physiological range of potential (−5 mV to −20 mV) where it can be either kept constant or changed (voltage-ramp mode) for the remaining period of the crystallization process. In addition, the pH and ionic content of the lipid matrix can be manipulated during crystallization. Membrane protein crystal formation occurs in a time frame of 24-96 hours depending on the membrane protein concentration and composition of the lipid matrix and the crystals are produced at room temperature or, if necessary, at lower temperatures. Also, lipid diffusion experiments can be performed to optimize crystal formation and quality.

An important feature of the invention is that when using a fluorescent tagged membrane protein the system will allow monitoring crystal formation and membrane protein stability during crystallization process. Moreover, Fluorescence Recovery After Photobleaching (FRAP) experiments can be used during the crystallization process to determine mobile fraction of the membrane protein and to optimize the lipid composition of the lipid matrix to achieve crystallization. It is important to point out that mobile fraction of membrane proteins in the lipid matrix will have to be over 75% to facilitate crystallization. Another important feature of the invention is that the system allows performing X-ray diffraction experiments in situ and that there is no limitation in the molecular weight (MW) of the protein, thus larger membrane complexes can be crystallized. This is extremely important since the invention overcomes the MW weight limitation that is intrinsic to the Lipidic Cubic Phase (LCP) methodology. The membrane protein crystal is harvested while the protein is grown at a sub-physiological membrane potential (−5 mV to −140 mV) and the membrane protein crystal is immediately frozen at −80° C.

The effectiveness of the present invention will be now explained in accordance to FIGS. 9-19.

Figure 9:
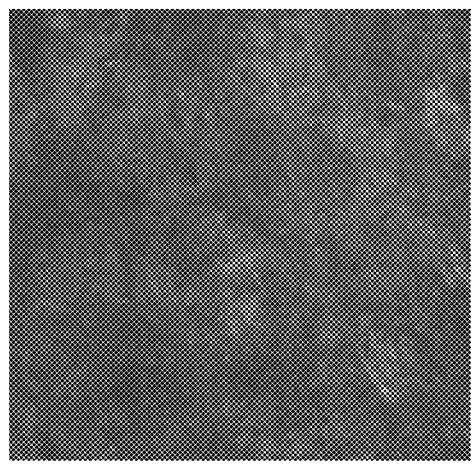
FIG. 9 shows images of protein samples without applying electric potential.
Figure 9:
Figure 10:
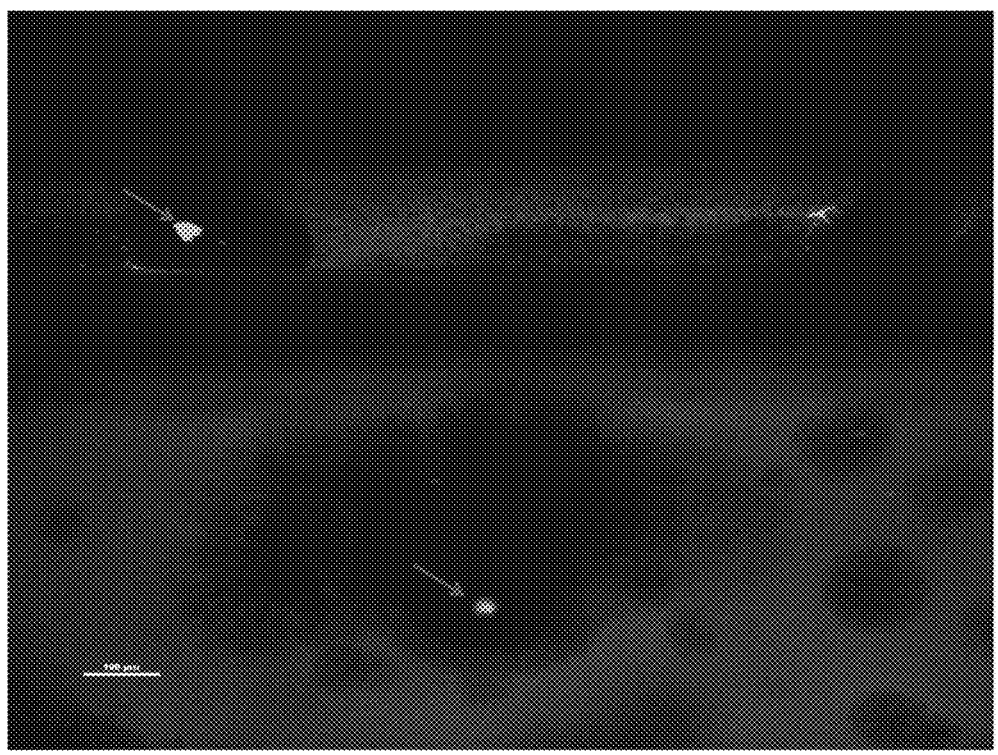
FIG. 10 shows images of protein crystals for a fluorescence-labeled protein according to an embodiment of the present invention.
Figure 11:
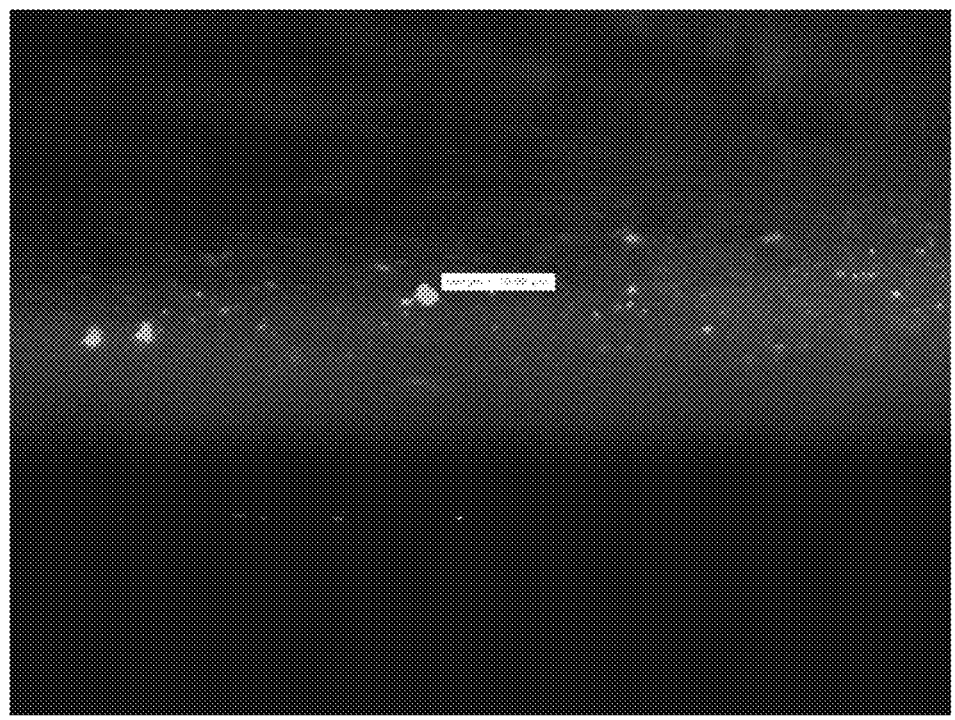
FIG. 11 shows images of a plurality of nAChR crystals inside the sample unit according to an embodiment of the present invention.
Figure 12:
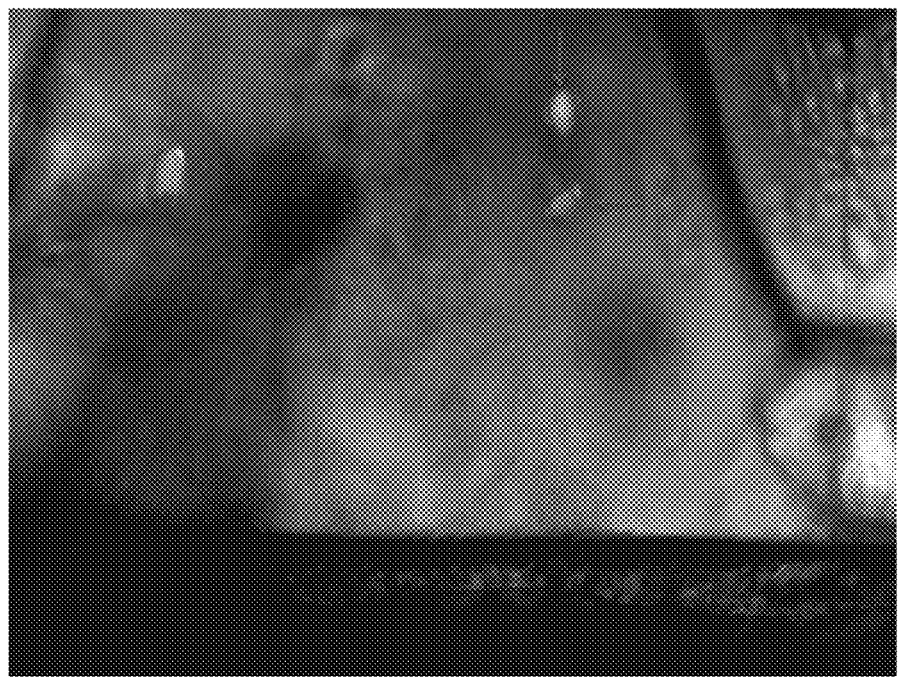
FIG. 12 shows images of a plurality of nAChR crystals inside the sample unit according to an embodiment of the present invention.
Figure 13:
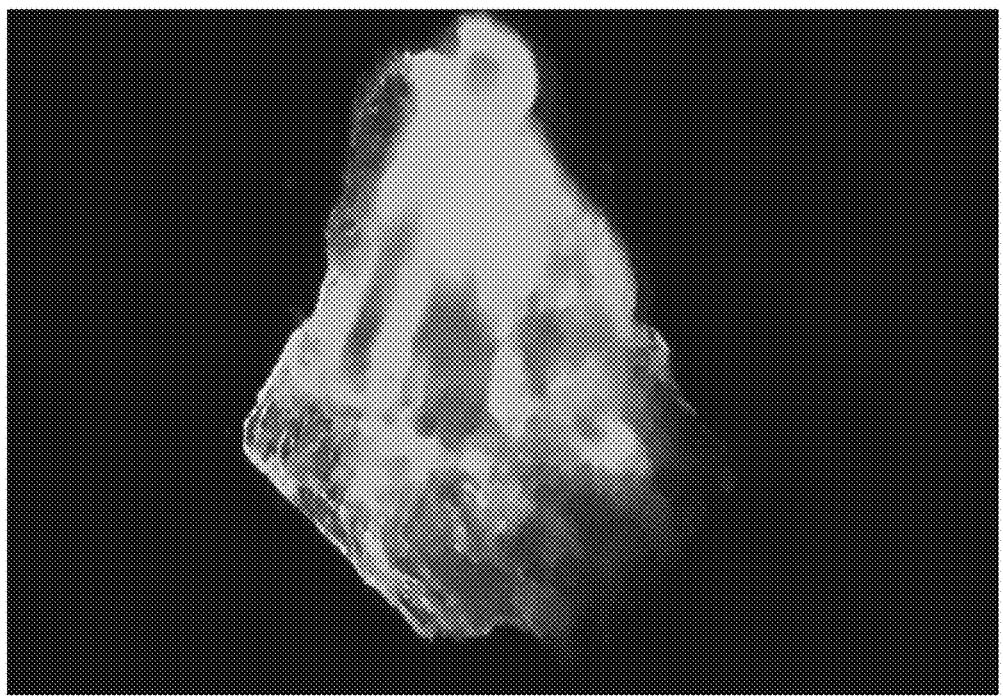
FIG. 13 shows a confocal microscopy image of a nAChR-αBTX crystal in the sample unit according to an embodiment of the present invention.
Figure 14:
FIG. 14 shows an image of a nAChR crystal in the loop according to an embodiment of the present invention.
Figure 15A:
FIG. 15a shows an image of a nAChR crystal in the sample unit according to an embodiment of the present invention.
Figure 15B:
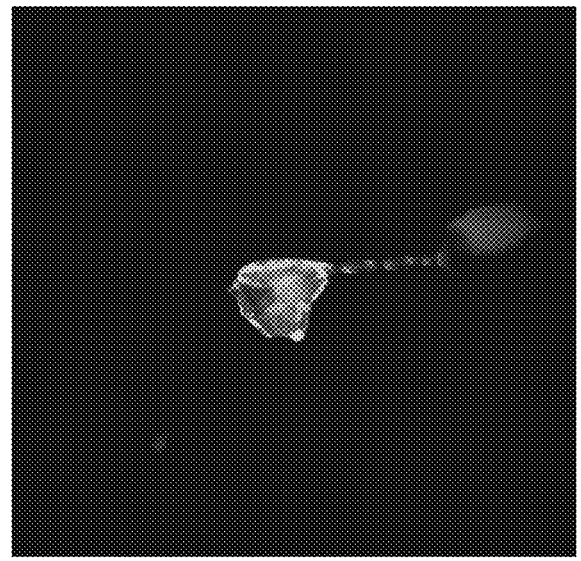
FIG. 15b shows an image of a nAChR crystal in the loop according to an embodiment of the present invention.
Figure 16A:
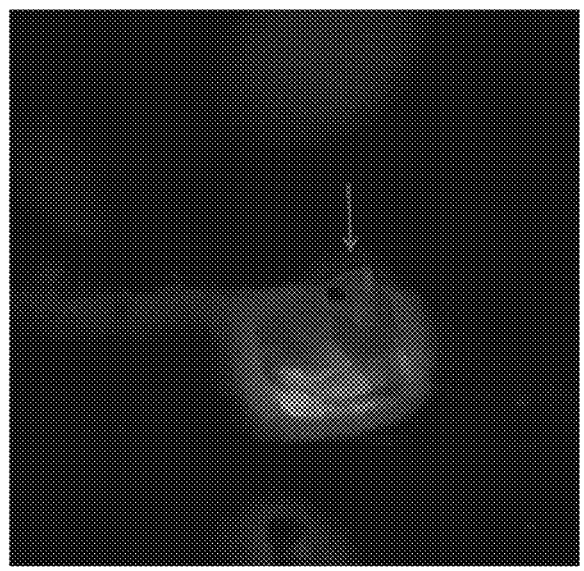
FIG. 16a shows an image of a nAChR crystal in the sample unit according to an embodiment of the present invention.
Figure 16B:
FIG. 16b shows images of a nAChR crystal in the loop according to an embodiment of the present invention.
Figure 17:
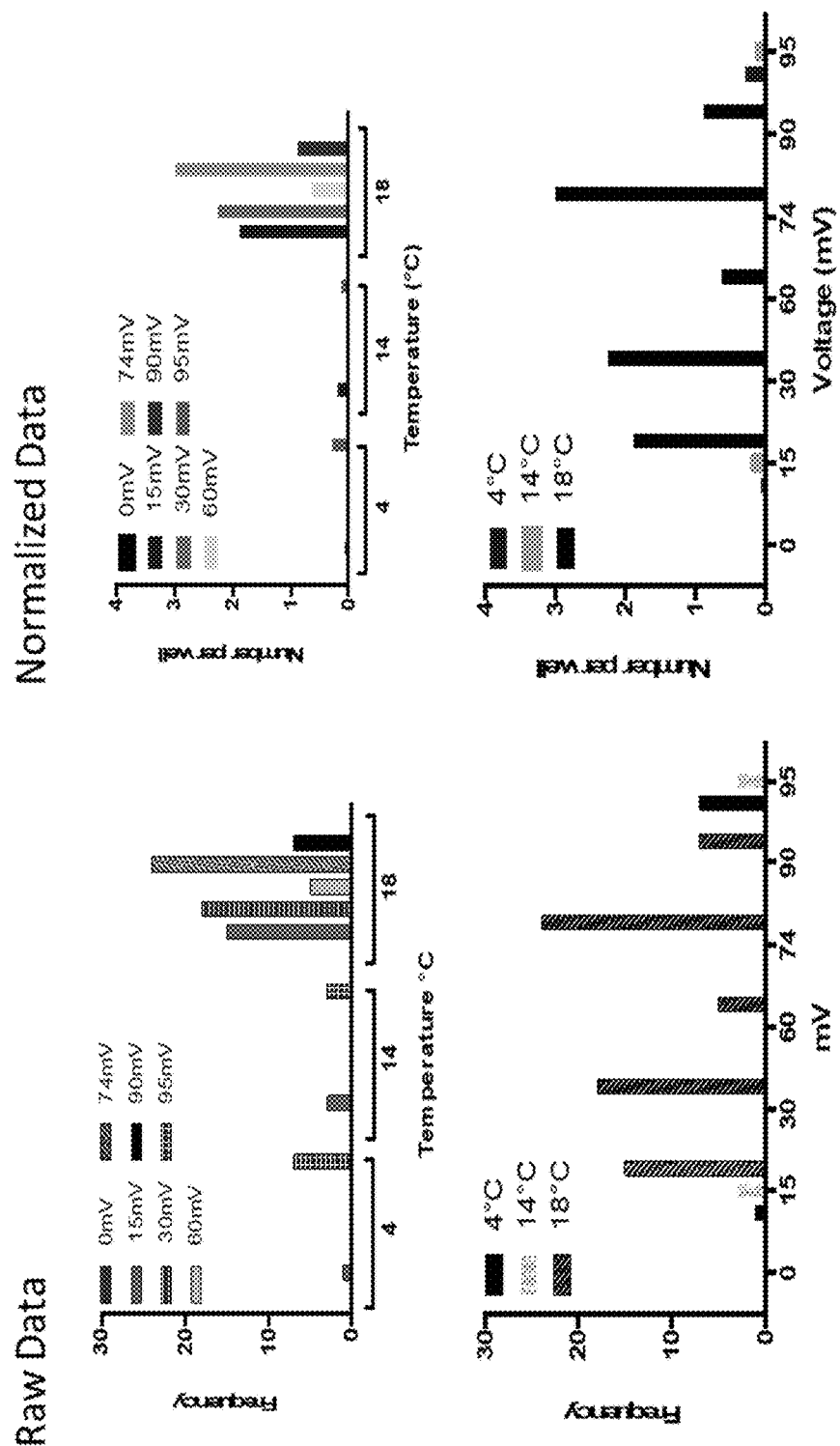
FIG. 17 shows histograms for protein crystal formation frequency distribution according to an embodiment of the present invention.
Figure 18:
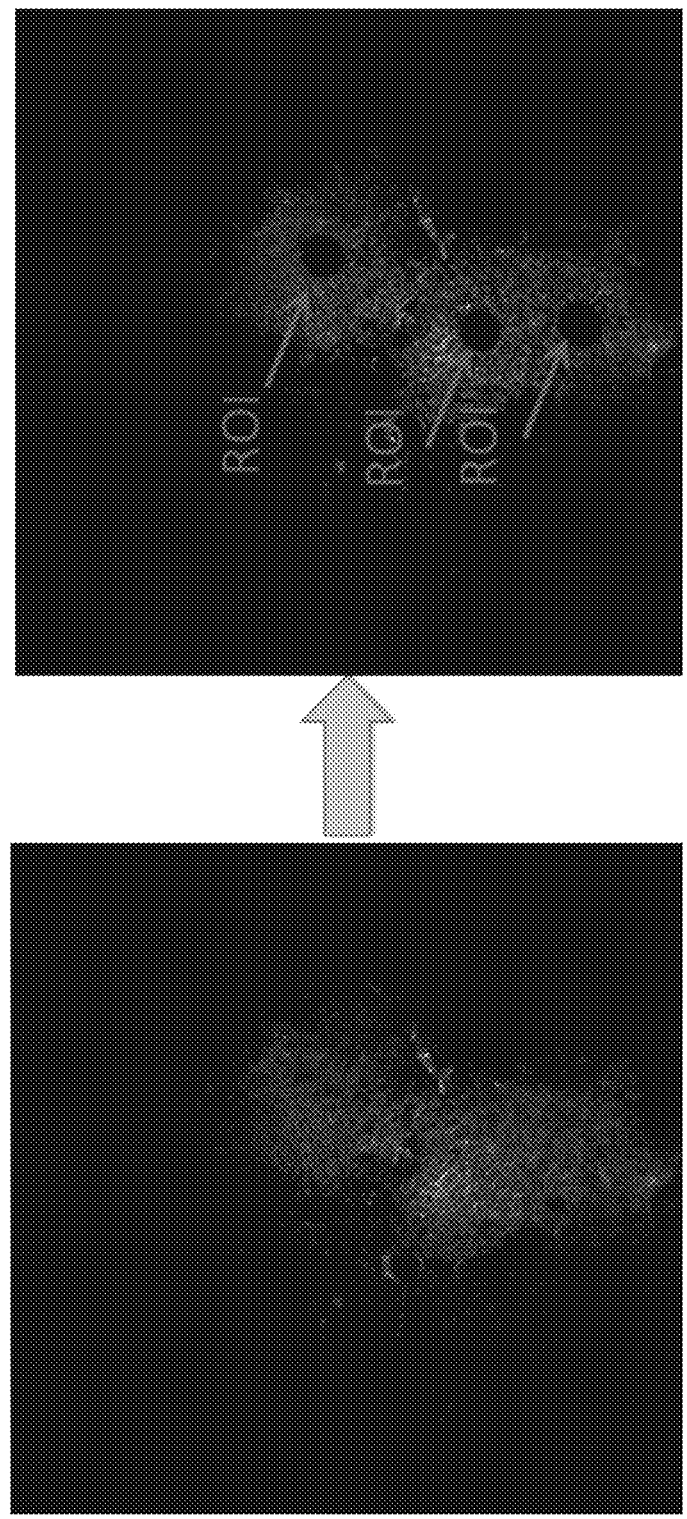
FIG. 18 shows images of protein crystallization using Voltage-Lipidic Cubic Phase-Fluorescence Recovery After Photobleaching technique according to an embodiment of the present invention.
Figure 19:
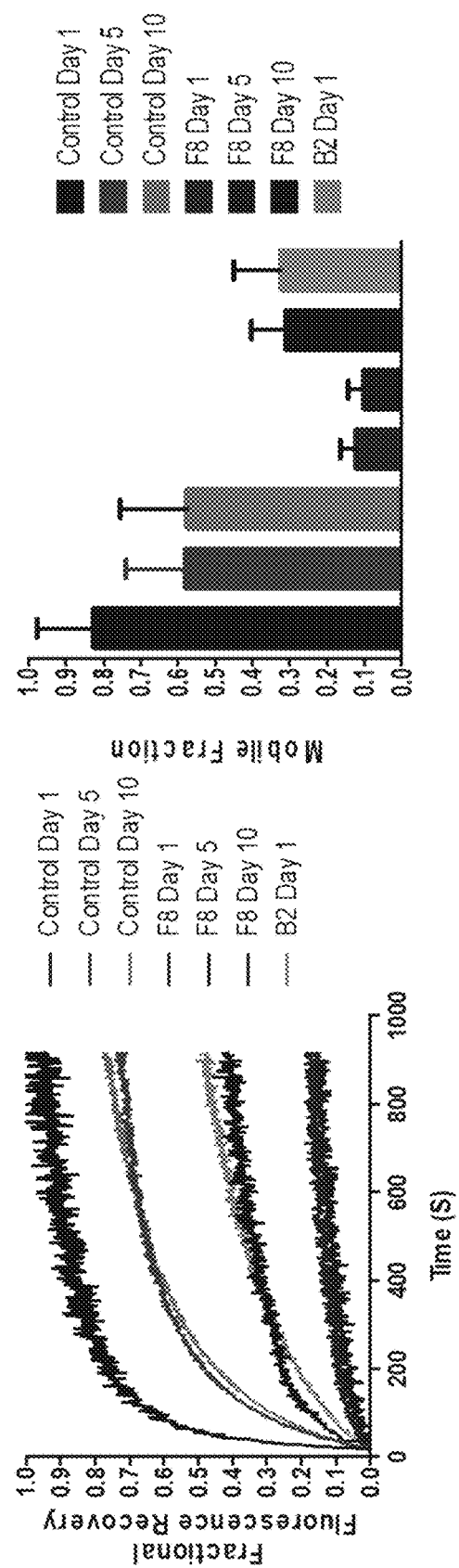
FIG. 19 shows fractional fluorescence recovery and mobile fraction plots for a Fluorescence Recovery After Photobleaching Assay according to an embodiment of the present invention.

FIG. 9 shows images of samples crystallization without applying electric potential according to the present invention. As can be appreciated, no well-formed crystals were found. In clear contrast FIG. 10 shows the formation of protein crystals, where nAChR is conjugated with a-Bungarotoxin Alexa Fluor® 488 for fluorescence and was prepared using a lipid cubic phase (LCP) technique (the arrows indicate the crystal formation). FIG. 11 shows several nAChR crystals growing in different sizes inside the sample unit according the present invention. FIG. 12 shows nAChR crystals formed from samples that were conjugated with α-BTX and monoclonal antibodies. FIG. 13 shows a confocal microscopy image of a well formed nAChR-αBTX crystal in the sample unit, where the crystal structure can be appreciated. FIG. 14 shows an image of a nAChR crystal (indicated by the arrow) in the loop ready to be diffracted. FIGS. 15a and 15b show images of a nAChR crystal in the sample unit (indicated by the arrow) and in the loop ready to be diffracted, respectively. FIGS. 16a and 16b show additional images of the nAChR crystal in the sample unit (indicated by the arrow) and in the loop ready to be diffracted, respectively. FIG. 17 shows histograms (for raw and normalized data) of protein crystal formation frequency distribution, where different voltages where applied for the stimulation of crystal nucleation and the sample size for the experiment was 160. FIG. 18 shows images of Voltage-Lipidic Cubic Phase- Fluorescence Recovery After Photobleaching Assay (V-LCP-FRAP) using a lipid cubic phase (LCP) in which the sample is placed in a lipidic and viscous environment. The Region of Interest (ROI) are the areas in which fluorescence recovery is measured. This assay was performed in order to determine which protein-detergent complexes provide the highest protein stability, for structural studies. FIG. 19 shows fractional fluorescence recovery and mobile fraction graphs for a FRAP assay experiment where lipidic cubic phase (LCP) was used. This experiment was carried out with the implementation of monoclonal antibodies in monoolein matrix for the nAChR-a-BTX complex using phospholipid analog detergent, where all experiments were performed in triplicate and the incubation was 20° C. and recorded every five days (three times for mAb-F8 and one time for mAb-B2).

A fundamental aspect of the present invention is the principle of membrane resistance. To this effect, the conditions for membrane protein crystal formation were assessed using a basic electrode prototype to determine the range of membrane potentials in which membrane protein crystals are formed in a defined lipid matrix composition using different electrode diameters. In a lipid matrix of define composition, crystal formation was observed within a resistance range of 1-25 MΩ depending on the protein concentration in the lipid matrix. The resistance range also depends on the size and molecular weight of the proteins because these are intrinsic parameters that affect the membrane capacitance. The resistance of the lipid membrane is critical to assure that ion flux is constant during the crystallization process. Our data shows that crystallization of membrane proteins can occur within a very limited range of sub membrane potentials.

The present invention overcomes the majority of the difficulties associated with vapor diffusion techniques (i.e, hanging drop, sitting drop, etc.), because the protein-detergent complex is rapidly mixed with a lipid matrix (LMx) of defined composition. Second, the detergent is immediately diluted in an enriched lipid matrix (LMx) where it diffuses from the protein-detergent complex in a native hydrophobic/aqueous environment allowing critical lipid-protein (and van Der Waals') interactions with the hydrophobic domains of the membrane protein. Third, the dilution and diffusion of the detergent from the protein-detergent complex under the aforementioned conditions is critical to preserve stability of the membrane protein and to reduce the aggregation caused by denaturation of protein hydrophobic domains. Fourth, during the process of detergent diffusion the membrane protein is presumably preserved in a single conformation by the membrane potential in LMx with constant resistance. Lastly, this methodology essentially reconstitutes the membrane protein in its native lipid environment under "cuasi" physiological conditions.

It is important to emphasize that the present invention provides a system and method where the membrane protein is transferred to a lipid matrix that holds a resting membrane potential, which reduces the degree of conformational freedom of the protein. The system and methodology led to consistent x-Ray diffractions from the nAChR-LFC16 complex. The invention will serve to test new approaches in a very challenging field of structural Biology and it represents a step forward in the use of innovative approaches for the solution membrane protein structures. This methodology was developed after many attempts to crystallize the nAChR using vapor diffusion methods and, more recently, LCP. Our team has being doing electrophysiological recordings of nAChR channel activity for many years and our basic understanding of the nAChR structure and function was conceptualized in a physiological environment. The system of the present invention was conceived to crystalize the nAChR in its closest physiological environment, which includes a native lipid composition and a fixed resting membrane potential.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the invention.

We claim:

1. A method for crystalizing membrane proteins comprising:
    adding a membrane protein sample to at least one holding well of a sample holding layer having a plurality of holding wells, wherein each holding well comprises a separate pair of electrodes and ensuring the membrane protein sample is in contact with both electrodes;

adding a crystallization precipitant solution to at least one lid well of a lid layer having a plurality of lid wells;

positioning said sample holding layer on top of said lid layer so that said at least one holding well lies on top and directly facing said a least one lid well a sample unit; and incubating said membrane protein sample by applying a voltage to the pair of electrodes of said at least one holding well at a predetermined temperature and at a predetermined humidity until said membrane protein sample is crystallized.

2. The method of claim 1, wherein said membrane protein sample comprises a solubilized membrane protein complex.

3. The method of claim 2, wherein said solubilized membrane protein complex is a solubilized protein-detergent complex.

4. The method of claim 1, wherein said membrane protein sample is incubated by placing said sealed sample holding layer inside an incubator that is maintained at said predetermined temperature prior to placing the sealed sample holding layer inside said incubator.

5. The method of claim 1, wherein said membrane protein sample is purified prior to being added to said at least one holding well.

6. The method of claim 1, wherein said membrane protein sample is provided in a lipid matrix.

7. The method of claim 6, wherein said lipid matrix has a variable impedance during the crystallization process.

8. The method of claim 1, wherein said membrane protein sample is subjected to a physiological membrane voltage at the beginning of the incubation process for an amount of time prior to being subjected to a sub-physiological membrane voltage.

9. The method of claim 1, wherein said voltage is maintained constant.

10. The method of claim 1, wherein said voltage has a variable waveform.

11. The method of claim 1, wherein said voltage is selected from a sub-physiological voltage, a physiological voltage and a supra-physiological voltage.

12. The method of claim 1, wherein said membrane protein sample comprises a fluorescent tagged membrane protein.

13. The method of claim 1, further comprising performing in situ X-ray diffraction experiments on said membrane protein sample.

14. The method of claim 1, further comprising performing Fluorescence Recovery After Photobleaching experiments on said membrane protein sample.

15. The method of claim 6, wherein said lipid matrix has a lipid composition similar to the lipid composition of the membrane protein in the native environment or is varied by lipid doping.

16. The method of claim 6, wherein pH and ionic content of the lipid matrix is adjusted prior to crystallization.

17. The method of claim 1, wherein the same voltage is applied to the pair of electrodes of all holding wells of said plurality of holding wells.

18. The method of claim 1, wherein different voltages are applied to the pair of electrodes of different holding wells of said plurality of holding wells.

19. The method of claim 1, wherein said plurality of holding wells contain membrane protein samples of the same member protein.

20. The method of claim 1, wherein said plurality of holding wells contain membrane protein samples of different member proteins.

21. The method of claim 1, wherein the membrane protein samples on said plurality of holding wells have the same protein concentration.

22. The method of claim 1, wherein the membrane protein samples on said plurality of holding wells have different protein concentrations.

23. The method of claim 1, further comprising incubating a plurality of samples units simultaneously.

24. The method of claim 1, wherein said lid layer comprises a plurality of lid wells having the same geometric configuration as said holding wells.

25. The method of claim 1, wherein the plurality of holding wells has the same geometric shape or different geometric shapes.

26. The method of claim 1, wherein the pair of electrodes have the same geometric shape in every holding well.

27. The method of claim 1, wherein at least one holding well has a pair of electrodes having a geometric shape different than the pair of electrodes of said plurality of holding wells.

28. The method of claim 1, wherein the holding wells have the same volume or different volumes.

29. The method of claim 1, wherein said voltage is a D.C. voltage.

30. The method of claim 11, wherein said sub-physiological voltage, said physiological voltage and said supra-physiological voltage are D.C. voltages.

* * * * *